United States Patent [19]
Gordon

[11] 3,936,607
[45] Feb. 3, 1976

[54] ELECTRONICALLY VARIABLE AUDIOMETER OF THE VON BEKESY TYPE

[75] Inventor: Sidney Gordon, New York, N.Y.

[73] Assignee: Michael Davis, Riverdale, N.Y.

[22] Filed: Nov. 28, 1973

[21] Appl. No.: 419,602

[52] U.S. Cl. .................................. 179/1 N; 323/74
[51] Int. Cl.² ........................................ H04R 29/00
[58] Field of Search ............. 179/1 N; 328/171, 169

[56] References Cited
UNITED STATES PATENTS
3,796,945  3/1974  Feldman et al. ...................... 323/74

Primary Examiner—Kathleen H. Claffy
Assistant Examiner—C. T. Bartz
Attorney, Agent, or Firm—Mandeville and Schweitzer

[57] ABSTRACT

The disclosure relates particularly to audiometers, such as used in ascertaining the hearing ability of test subjects. Functionally, the new audiometer is similar to the so-called von Bekesy audiometer. However, the new system incorporates unique and advantageous circuit arrangements which enable controlled variable attenuation of a power signal to be achieved through simple and reliable electronic means. The new system eliminates the costly and fast-wearing electro-mechanical mechanism customarily used and heretofore considered necessary in a von Bekesy audiometer. The new electronic attenuation system includes means, effective in the extremely low power range of audiometer signal generation, to apply a high level, controllably variable signal, and to attenuate that signal across a high ratio voltage divider. In the high power ranges of the audiometer, the generated signals need not be attenuated in the first instance, and the voltage divider is rendered ineffective automatically when the system operates in the higher ranges. A current amplifier supplies the necessary additional current requirements for high level signals.

The new system is unique in its ability to generate an extremely low power adiometer signal by electronic means while effectively obviating the problem of unfavorable noise-to-signal ratios in the low power ranges.

15 Claims, 1 Drawing Figure

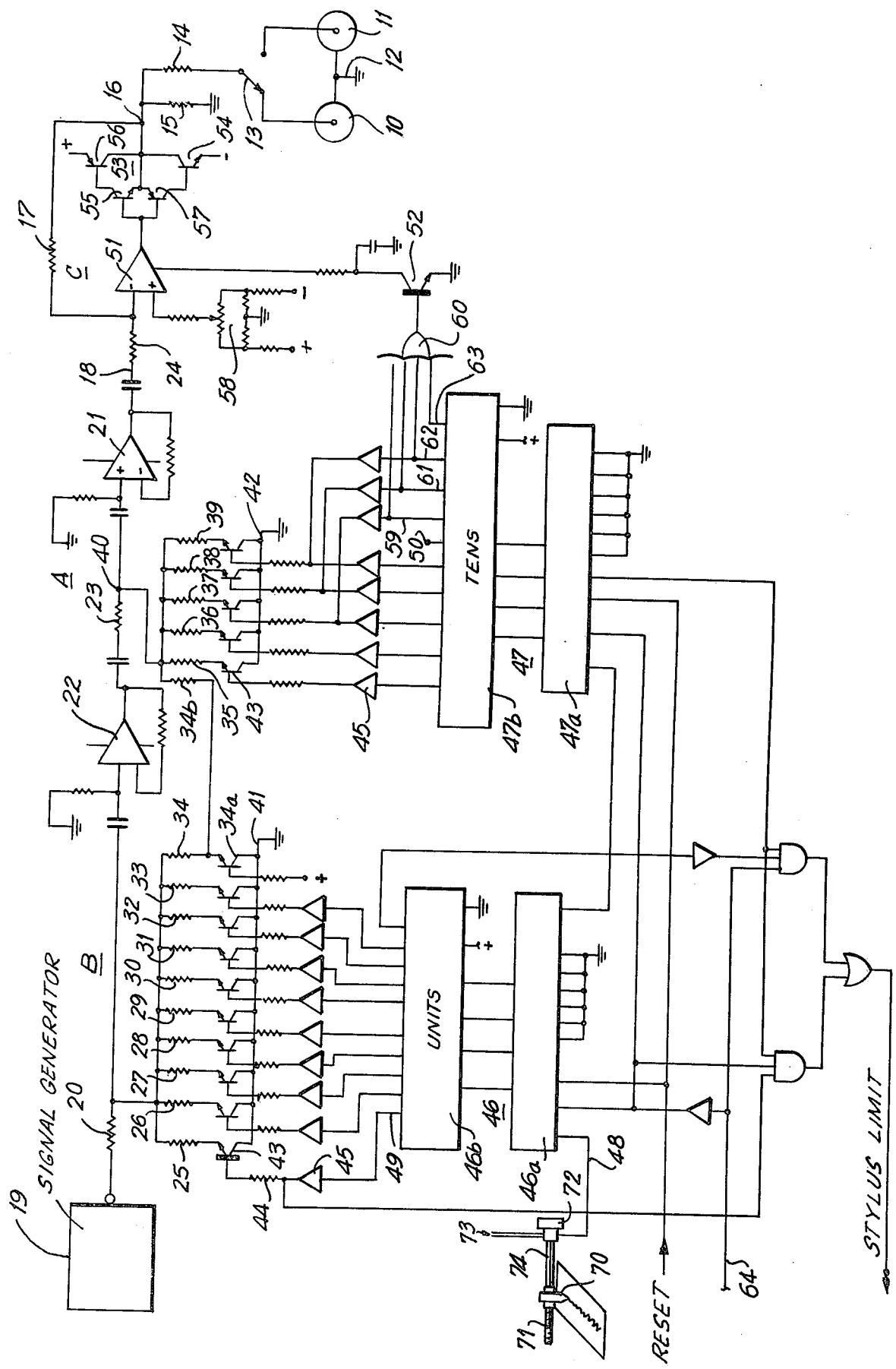

ELECTRONICALLY VARIABLE AUDIOMETER OF THE VON BEKESY TYPE

BACKGROUND AND SUMMARY OF THE INVENTION

This invention relates particularly to audiometer systems, for use in determining the hearing capability of test subjects. Conventional clinical audiometers are commonly constructed in accordance with the basic principles of the von Bekesy U.S. Pat. No. 2,563,384. The von Bekesy system comprises a variable frequency acoustical generator, the output of which is connected to a variable resistance network. The variable resistance network conventionally includes a contact slide which is positioned along the resistance network by means of a reversibly driven electric motor. The resistance network desirably has a logarithmically variable output as a function of linear variation in the position of the contact slide.

In the conventional von Bekesy type audiometer system, an input signal is generated at a predetermined frequency, and the test subject actuates the drive motor for the contact slide, causing the power level of the applied signal to be controllably varied. Initially, the applied signal is subject to maximum power attenuation by the resistor network. However, by appropriate actuation of the drive motor, the slide is caused to move along the network, progressively reducing the signal attenuation, until the subject is first able to hear an audible sound, typically applied through a set of headphones. After hearing the first sound the subject actuates a switch to reverse the slide-positioning motor. This causes progressively increasing attenuation of the signal, until no sound is heard, at which time the subject again reverses the slide-positioning motor. This process of motor reversal is continued for a short period of time, permitting a rather accurate observation to be made of the subject's hearing threshold at a given frequency.

Usually, the contact slide for the resistance network is coupled with a tracing pen and a moving chart, so that a continuous graph is drawn of the movements of the contact slide. By proper calibration of the chart, an accurate graph, reflecting the hearing capability of the subject, is automatically prepared, as the subject successively reverses the slide positioning motor.

The von Bekesy type purpose system has proven to be effective for its intended purposes and has been widely adopted for clinical testing. However, it suffers the disadvantage that the electro-mechanically variable atttenuation system, comprising a motor driven contact slide and related elements, is a very expensive unit. It must be manufactured with great precision and must be carefully maintained; it represents a significant cost factor in the complete audiometer. Although it is well known, as a generality, that electronic means frequently can be substituted for electro-mechanical systems, it has nevertheless been considered impracticable to provide electronic attenuation in an audiometer, because of the extreme wide range of power output required (typically 100 decibles) and the rather stringent requirements regarding the purity of the output at the lower power levels. Thus, at the lowest levels of output, an audiometer may require a signal voltage on the order of a fraction of a micro-volt. However, even in the highest quality solid state circuits, the electronic "noise" may be as much as a micro-volt, so that the low level signals would be masked by the noise. Inasmuch as clinical audiometers are required to be effectively free of noise, a condition cannot be tolerated in which the noise represents even a substantial fraction of the signal voltage.

The present invention provides a unique and advantageous electronic attenuator system which is entirely suitable for use in clinical audiometers and which is substantially less expensive and more reliable and durable than conventional electro-mechanical attenuators.

In accordance with the present invention, a von Bekesy type audiometer is provided, in which the conventional electro-mechanical attentuator is replaced by a novel system of selectively operable resistance combinations, actuated in predetermined sequence by a source of timed pulses, synchronized with a recording device, in conjunction with an up/down decade counter system actuated by the pulse source. When the attenuator system is in operation, the attenuation of a predetermined input signal is controlled by successively connecting into circuit a series of control resistors to effect incremental changes in the voltage level of the applied signal. By appropriate selection of resistor values, the incremental changes in voltage may be controlled to suit the specific application. In the case of a clinical audiometer, incremental changes of one decibel are desirable. To accomplish this, the circuit of the invention includes a novel arrangement of attenuator control resistors effective in increments of ten decibels and increments of one decibel, enabling the entire power range to be covered in units of one decibel.

Because of the enormous power range required in a clinical audiometer (0–100 decibels, typically) circuit requirements in the lower end of the power range are significantly different from the circuit requirements in the higher end of the power range. To accommodate effectively these different requirements, the system of the invention provides for the supply of an input signal, at an effective power level in mid-region of the overall power range but at a voltage level at the maximum level required at the system output. This input signal, controllably attenuated in accordance with a predetermined sequence, is applied to a high ratio voltage divider formed in part by the system output, typically a set of headphones. By providing for the signal applied at the voltage divider to be a large multiple of the signal applied to the headphones, it is possible to effectively mask the electronic noise which is inherent in the solid state electronic sequencing system employed in conjunction with the attenuator control resistors.

In accordance with an important aspect of the invention, novel circuit arrangements are provided for achieving power output levels in the higher ranges, extending from the predetermined mid-range level to the level of the desired maximum power output. To this end means are provided for effectively eliminating from the output circuit the high ratio voltage divider, so that the maximum effective voltage is made available at the output stage of the system. Moreover, since the current requirements at the higher power levels are enormously greater than in the lower power ranges, the novel circuitry of the system includes means for amplifying the input current and thereby supplying the necessary output current requirements without overloading or unbalancing the attenuator system.

In a specific embodiment of the invention intended especially for clinical audiometers, the input signal is applied to the voltage divider circuit at a maximum level (assuming no attenuation) sufficient to provide the equivalent of a 60 decibel output at the headphones. The new circuit arrangements include means operative, when actuated, to effectively eliminate the high ratio voltage divider, making available an increased signal voltage, 40 decibels greater, providing a maximum effective output voltage level of about 100 decibels. An appropriate current amplification is also introduced at this stage. Progressively varied attenuation of the input signal level is effected through primary and secondary voltage attenuating resistance networks. The primary network includes a main resistor, which is selectively connected to ground through any one of five attenuator control resistances, forming voltage divider combinations corresponding to voltage level attenuation of −50 to −10 decibels. The secondary network also includes a main resistor which is selectively connected to ground through any of a series of resistors, forming voltage divider combinations corresponding to attenuation levels of −10 to −1 decibels. By appropriate selection of control resistances in these primary and secondary networks, any level of attenuation may be achieved from 0 to −60 decibels, in increments of one decibel.

In the power output range from 99 decibels to 60 decibels, incremental attenuation is achieved by appropriate selection of control resistances in the two networks, in conjunction with actuation of an amplifier circuit which effectively eliminates the high ratio voltage divider and thus effectively makes available 40 decibels of voltage to the output. Thus, activation of the amplifier system in conjunction with variable attenuation of the incoming signal of up to −40 decibels from its maximum will provide the necessary incremental attenuation in the 60–99 decibel output range.

Because of the enormous increase in power requirements in the upper power ranges, the amplifier circuit which becomes effective at the 60 decibel level, includes a current amplifier operative to supply the additional current flow. Significantly, the operation of the amplifier circuit is such that the amplifier cannot, under any circumstances, self bias to a conductive state. Accordingly, when the system is operated in the lower power ranges, the amplifier system does not contribute electronic noise to the system output.

For a better understanding of the above and other features and advantages of the invention, reference should be made to the following detailed specification and to the accompanying drawing.

DESCRIPTION OF THE DRAWING

The single sheet of drawings comprises a highly simplified schematic representation of an electronic attenuation system incorporating the features of the invention, as utilized to advantage in a clinical audiometer.

DESCRIPTION OF PREFERRED EMBODIMENT

Referring to the drawing, the reference numerals 10, 11 represent left and right side headphone units of an audiometer. The drive coils (not specifically shown) for these headphone units are connected to ground at 12. The other side of the drive coil for each headphone unit is selectively connected to the power circuit through selector relay contacts 13 and 10 ohm resistor 14.

In a typical system, each of the headphones 10, 11 may have an effective impedance of 10 ohms, so that the combination of a headphone coil and the resistor 14 in series forms a resistance of 20 ohms. This combination is connected in parallel with a 20 ohm resistor 15, so that output of the system between junction point 16 and ground has effective resistance of about 10 ohms. Resistors 17, 24, each of about 500 ohms, are connected in series with the resistors 14, 15. The overall circuit resistance between circuit point 18 and ground is approximately 100 times the resistance between circuit point 16 and ground, such that the output end of the system, between circuit point 18 and ground can be utilized in accordance with the invention, as a high ratio (100:1) voltage divider, designated by the reference letter C.

In accordance with the invention, a predetermined input signal is supplied by a signal generator 19, forming no part of the invention, which supplies an input signal at selected frequencies and at a predetermined maximum voltage level. This signal is applied through primary and secondary attenuating resistor networks A, B, including respective isolating amplifiers 21, 22 to the circuit point 18. The amplifiers 21, 22 are connected to provide unity gain, with no attenuation, and thus function merely to isolate successive stages of the circuit.

In an advantageous circuit arrangement according to the invention, the signal applied by the signal generator 19, assuming no controlled attenuation of the signal, is intended to provide maximum voltage (approximately 100 decibels) at the headphones 10, 11. In this respect, however, an important feature of the invention resides in the fact that in the low power range, voltage is applied to the headphones through the high ratio voltage divider circuit C previously described, so that the signal voltage level available at circuit point 18 is larger by a factor of 40 decibels than the voltage applied to the headphones.

A controlled variable attenuation of the input signal is provided, in accordanc with the invention, by the attenuation networks A, B. These networks selectively connect attenuating resistors 20, 23 to one or a combination of attenuator control resistances 25–34 and 35–39, forming attenuating voltage dividers. The resistors 25–34 form part of the secondary network B and, when connected in series with the resistor 20 in a one-at-a-time sequence, will result in signal attenuation in increments of 1 decibel. In a typical circuit according to the invention, the network resistor 20 may have a resistance in the order of 10,000 ohms, while the control resistors 25–34 may range in resistance from about 30,000 ohms in increments down to about 5,000 ohms. When the first control resistor 25 is connected between the resistor 20 and ground, resistors 20, 25 will form a voltage divider providing signal attenuation of 10 decibels. With resistor 26 in series, signal attenuation will be nine decibels; and likewise, by connecting the other resistors 26–33 in series, in sequence, increased attenuation is provided in increments of one decibel. Control resistor 34 is constantly connected to ground and, when resistors 25–33 are not connected, provides attenuation of one decibel.

The control resistors 35–39 constitute part of the primary network A for effecting signal attenuation in major increments, desirably in 10 decibels. Thus, when the resistor 35 is connected (at circuit point 40) in series with the resistor 23, a voltage divider is formed which provides a 50 decibel attenuation. With the resistors 36–39, individually connected in series with the resistor 23 (typically of 1 megohm) control resistance values are calculated to achieve signal attenuation of 40, 30, 20 and 10 decibels respectively.

As will be appreciated, by appropriate selection and connection in circuit of control resistors of the respective attenuating networks A and B, the 100 decibel incoming signal may be attenuated in any amount up to 60 decibels, in increments of one decibel. For operation in low power ranges, the high ratio voltage divider network C provides an additional 40 decibels of attenuation. In typical audiometer applications, the controllably variable attenuation is achieved in progression, usually commencing with maximum attenuation (minimum power at the headphone) and progressing in increments of one decibel until a test subject wearing headphones first begins to detect audible sounds at the selected input frequency.

In accordance with the one aspect of the invention, the various attenuator control resistors 25–34, 35–39 are selectively connected to a ground conductor 41 or 42 by means of individually controlled switching transistors identified by the reference numeral 43. To advantage, groups of these transistors may be derived from conventional integrated circuit elements. In one advantageous embodiment of the invention, the switching transistors are derived from RCA 3082 integrated circuit units, providing a plurality of NPN transistor elements 43. These transistor elements are arranged for operation in an inverted alpha mode to provide minimum offset voltage drop across the transistor when in an "on" condition. The emitter electrodes of the transistors are connected to the respective control resistors 25–34, 35–39 and the collector electrodes are connected to the common ground 41, 42. The base electrodes of the several switching transistors are connected through current limiting resistors 44 and inverters 45 to counter-convertor units 46 or 47. In the illustrated circuit, the counter-converter unit 46 is associated with the switching transistors for control resistors 25–34, for "unit" increments of attenuation, and the counter-converter unit 47 is associated with the switching transistors for resistors 35–39, providing attenuation in increments of ten decibels.

In one advantageous embodiment of the invention, the counter-converter units 46, 47 include up/down decade counters 46a, 47a, which may be the type bearing the standard code designation no. 74190. The up/down decade counters 46a, 47a, are respectively connected to BCD to decimal converters 46b, 47b, which may be of the type bearing the standard code designation 7442. The illustrated counter-converter units 46 and 47 provide for an initial pulsed input to be converted to coded binary form, by the up/down decade counters. The binary output is converted to decimal form by the BCD to decimal converters.

Input for the counter-converter unit 46 is a controlled pulse source, to be described. When the equipment is in operation, a series of controlled pulses in supplied to the up/down decade counter 46a, causing it to progress through a sequence and causing the associated BCD-to-decimal converter 46b, to provide successive triggering signals, one at a time and in sequence, at each of ten output terminals 49. The tenth input pulse to the "ones" up/down counter 46a, will recycle the counter and also supply an input pulse to the up/down counter 47a, for the "tens" attenuating network 47.

In accordance with one aspect to the invention, where the system is used as an audiometer, reliable synchronization of the attenuating circuitry with the physical position of a chart recording stylus is assured by deriving actuating pulses for the up/down counter 46a directly from stylus motion. To this end, a stylus 70 may be positioned by means of a threaded shaft or the like 71. The shaft 71 is driven by a stepping motor 72 actuated in predetermined rotational increments by input pulses from an external source 73. The input pulses typically are controlled by test subject, as will appear. A shaft encoder unit 74 is associated with the threaded shaft 71 and, in response to each rotational increment of movement imparted by the stepping motor 72, will supply a signal pulse which is directed to the decade counter 46a through conductor 48. In this manner, input pulses to the attenuator control circuit are derived only from actual movements of the stylus drive, so that there is always exact correspondence between the stylus position and the condition of the attenuator circuitry. Any errors in the translation of input pulses from the external source 73 into stylus motion will not cause the attenuator circuitry to become out of phase or out of synchronization with the recording stylus 70.

At the outset of operation, a positive voltage signal is provided at the left hand output terminal of counter-converter unit 46, rendering conductive the switching transistor for resistor 25 and connecting it to ground. With each incoming pulse from the stylus drive, the positive signal is shifted one terminal to the right, so that each of the transistors is rendered conductive one at a time and in sequence, until the first nine have been activated. The tenth resistor 34 is at all times connected to ground through always conductive transistor 34a. After the tenth pulse of each series, only the resistor 34 is in circuit, providing an attenuation of −1 decibel. With the next incoming control pulse, the "ones" counter-converter 46 actuates the "tens" counter-converter 47 and returns to the beginning to connect in circuit the first resistor 25 to commence a new cycle.

According to the contemplated operation of the illustrated equipment, the "tens" counter-converter 47 will, at the outset, provide a positive control signal at its left terminal, connecting the control resistor 35 (−50 decibels) to ground. Thus, initially, resistors 25, 35, constituting a total attenuation of 60 decibels, will be connected in circuit. The −50 decibel resistor 35 remains in circuit throughout one complete cycle of the "units" counter-converter 46. When the counter-converter 46 commences to recycle, the shift signal is transmitted to the up/down decade counter 47a, causing the "tens" counter-converter unit 47 to provide a positive control signal at its second terminal. This disconnects the resistor 35 and connects resistor 36, representing an attenuation of −40 decibels. As will be readily understood successive cycling of the "units" counter-converter 46 will cause progressive advancement of "tens" counter-converter 47, so that the input signal attenuation will progress in 1 decibel steps throughout the range of the attenuator system.

In the illustrated arrangement, after the fifth cycling of the "units" counter-converter 46, the output signal of the "tens" counter-converter is at a blind terminal 50, so that none of the "tens" resistors 35–39 are connected in circuit, and the attenuation is provided exclusively by the resistors 25–34.

By the constant connection to ground of the resistor 34, a constant bias is provided for the control resistors 25–33. In a like manner, a high value resistance 34b is connected to ground through the transistor 34a, providing bias for the several resistors 34–39 of the primary attenuating network A. Connecting the resistors 34, 34b, to ground through a constantly conductive transistor 34a, rather than through a direct connection, provides a more constant bias, because the transistor 34a, forming a portion of an integrated circuit including several of the transistors 43, "tracks" with the other transistors with respect to changes in characteristics resulting from variations in temperature, voltage, etc.

Because of the electronic noise inherently and unavoidably present in the switching transistors and other solid state components, it is a feature of the invention that the attenuated signal made available at the circuit point 18 is greater by a large multiple than the signal required at the headphones 10, 11, and this signal is applied across the 100:1 voltage divider network C to achieve the desired power level at the headphone. By this means, the signal-to-noise ratio of the signal available at the circuit point 18 may be very high, and the noise is then effectively suppressed at the headphones. However, to attempt to utilize these principles of operation over the entire 100 decibel power range of the equipment would place enormous demands on the system in the higher power ranges, where the signal-to-noise ratio does not present a serious problem in the first instance. Accordingly, as an important feature of the invention, novel and advantageous means are provided for effectively eliminating the attenuating effect of resistors 17, 24 of the voltage divider C. The voltage made available at the circuit output point 16 is thereby increased by a factor of 100, corresponding to +40 decibels, relative to the voltage as attenuated by the divider network. The system can thus provide for the availability of the desired 100 decibel signal at the output.

According to the invention, the power control means provided for effectively eliminating resistors 17, 24 from the output circuit comprises an operational amplifier arranged for unity gain. In the illustrated arrangement, this includes a 8021 solid-state amplifier 51, connected in series with the 500 ohm resistor 24 and in parallel with the 500 ohm resistor 17. An NPN transistor 52 controls the functioning of the amplifier 51. When the transistor is non-conductive, the amplifier is off and no current flows. When the transistor 52 is rendered conductive, the amplifier 51 is biased on. When the amplifier is operating, resistors 24, 17 are effectively eliminated from the circuit. The amplifier circuit also includes, according to the invention, a current amplifier 53, comprising a pair of NPN transistors 54, 55 and a pair of PNP transistors 56, 57. The amplifier 51 is connected to the base electrodes of the transistors 55, 57, while the base electrodes of transistors 56, 54 are connected to the collector electrodes of the transistors 55, 57. The emitter of the transistor 56 is connected to a source of positive supply voltage and the emitter of the transistor 54 is connected to a negative supply voltage.

When the amplifier control transistor 52 is rendered conductive, the amplifier 51 is activated to its "on" condition, effectively removing resistors 17, 24 from the system output. The current amplifier 53 is designed to provide sufficient current capacity to satisfy the increased current requirements providing for the desired significant increase in output power without overloading and unbalancing the variable attenuator stages A and B of the system.

When the amplifier control transistor 52 is in a non-conductive state, bias current is removed from the amplifier 51. At these times, the amplifier 51 is "off" and no current can flow. Thus, in the low power mode of the system, there is no electronic noise contribution from the amplifier circuit components.

Desirably, there is a suitable zero adjust network 58 associated with the unity gain amplifier 51 to correct for any zero offset.

In accordance with the invention, the amplifier 51 is automatically rendered operative when the "tens" counter-converter 47 shifts into the range corresponding to a desired system output of 60–99 decibels. Thus, after the sixth cycle of the "units" counter-converter 46, the "tens" counter-converter will present a signal at terminal 59. This will simultaneously connect into circuit the resistor 37 (−30 decibels) and, through a gate 60, render conductive the transistor 52 to energize the amplifier circuit making available a 40 decibel signal gain at the output by reason of effectively eliminating or by-passing the voltage divider resistors 17, 24. The combination of a 30 decibel attenuation and a 40 decibel effective gain will provide a signal of 70 decibels at the output. The combination of a 40 decibel effective gain from the power amplifier circuit, a 30 decibel attenuation through resistor 37 and a 10 decibel attenuation through resistor 25 will provide for an effective signal of 60 decibels at the output, and this will increase in steps of 1 decibel, to 69 decibels, as the "units" counter-converter 46 goes through its cycle.

In continued sequence, the "tens" counter-converter 47 will activate terminal 61, connecting in circuit the resistor 38 (−20 decibels). The amplifier circuit remains operating through a signal applied at gate 60. After another complete cycle of the "units" counter-converter 46, terminal 62 of the "tens" counter-converter 47 is activated, and after still another cycle, terminal 63 is actuated, maintaining an "on" signal at the amplifier circuit but providing no attenuation by the resistors 35–39. In this unique and efficient manner, it is possible to provide the desired high level power to the headphones 10, 11.

In typical operation of the system of the invention, the headphones 10, 11 are placed on the test subject, and the selector relay 13 is actuated to be connected to either the right or left side transducer. The signal generator 19 is set to provide the desired frequency. Operation of the system is then placed under the control of the test subject through a control switch input identified by the reference numeral 64. When the subject is ready, the system is actuated and commences a sequencing of the variable attenuator, starting from full attenuation (0 decibel output) and progressing in 1 decibel increments through increasingly higher levels of power output. Eventually, a typical test subject will be able to detect an audible sound at the headphone, and immediately will actuate the input control 64, to cause the up/down counters 46a, 47a, to begin to sequence in reverse. During the reverse sequencing of the counters, the signal attenuation increases in 1 decibel steps. As soon as the test subject is no longer able to detect an audible sound at the headphone, he again reverses the direction of sequencing of the counters. This process of reversal is continued for a suitable interval, enabling a reading of satisfactory accuracy to be obtained as to the test subject's threshold of audibility for a signal of given frequency. Suitable means are provided for inhibiting operation of the up/down counters 46a, 47a, at the 0 and 99 decibel levels, the limits of the desired range of a typical audiometer.

As previously described, the test subject controls the movements of a stepping motor 73 associated with a stylus 70. Pulses to the up/down counter 46a are derived from the shaft encoder 74, such that the stylus motions necessarily are in exact correspondence with the sequencing of the electronic attenuator providing an accurate graphic representation of the responses of the test subject.

The system of the invention enables substantial economies to be realized in the manufacture of audiometers and similar devices, by completely eliminating the need for employing a precision electro-mechanical adjustable attenuator resistance network. Such electro-mechanical attenuator mechanisms represent a significant cost factor in the production of conventional audiometers, and yet such devices have rather poor reliability and durability.

The replacement of electro-mechanical devices by the electronic system of the invention enables important production savings to be realized. This is of particular significance from a practical, commercial viewpoint, because of the accelerating tendency toward industrial utilization of audiometers in connection with employee health programs and the like. For typical industrial utilization not only the cost factor is of great significance, but of possibly even greater importance is the dependability and useful life of the equipment when utilized under industrial, as distinguished from laboratory, conditions. In this respect, the system of the invention utilizes solid state electronic components, the longevity and dependability of which is well established, to replace the rapidly-worn, high cost, precision mechanisms of the conventional units.

A fundamental feature of the invention resides in the utilization of a two-stage attenuation technique, which enables a high level signal to be applied in the lower power ranges, for effective suppression or masking of the electronic noise which is inherent in a system utilizing transistor switching devices. This high level controllably attenuated signal is applied over a high ratio voltage divider, so that a signal of the appropriate level is derived at the headphones. In the higher power ranges, the inherent electronic noise is, percentagewise, not a significant consideration. Accordingly, the system of the invention uniquely provides for the effective elimination of the attenuation otherwise provided by the high ratio voltage divider.

As a further significant feature of the invention, the circuit arrangement providing for effective elimination of the voltage divider includes a current amplifier of sufficient capacity to supply the increased current requirements of the output load. This enables the necessary high level outputs to be delivered to the headphone without overburdening the first stages of the circuit with unduly heavy current flow conditions.

It should be understood, of course, that the specific form of the invention herein illustrated and described is intended to be representative only, as certain changes may be made therein without departing from the clear teachings of the disclosure. Further, although the invention is known to be highly advantageous for use in connection with audiometer equipment, the underlying principles of the invention may have substantially broader utilization. Accordingly, reference should be made to the following appended claims in determining the full scope of the invention.

I claim:
1. An electronically sequenced power attenuator system for a clinical audiometer or the like providing a wide range of attenuation and a substantially noise-free signal at all levels, which comprises
   a. means for generating an input signal of predetermined voltage level,
   b. electronically variable attenuation means for controllably attenuating said signal from said predetermined level to a level which is a sufficiently large multiple of the desired output level that the signal to electronic noise ratio permits intelligible, audible reproduction of the signal,
   c. voltage divider means connected to the attenuator means and including output resistance means which is a small fraction of the effective resistance of the voltage divider corresponding to an inverse of said large multiple, and
   d. power control means automatically operative at all levels of output signal above a predetermined level to effectively by-pass a portion of said voltage divider means.
2. The system of claim 1, further characterized by
   a. said system forming part of an audiometer system of the von Bekesy type having a variable power output of in the 100 decibel range,
   b. said voltage divider providing a ratio of input to output voltage of in the range of 100-to-1, and
   c. said power control means being automatically operative at a predetermined level of output signal.
3. The system of claim 1, further characterized by
   a. said power control means comprising a unity gain operational amplifier, including a transistor-type current amplifier.
4. The system of claim 1, further characterized by said electronically variable attenuator comprising
   a. voltage divider means connected to said signal generating means and including a first common resistor,
   b. a plurality of attenuation control resistors selectively connectable between said common resistor and ground,
   c. a separate switching transistor connected in series with each of said control resistors for connecting said resistors in circuit and thereby controllably regulating voltage drop across said common resistor, and
   d. time-sequenced control means for rendering said transistors conductive in predetermined time sequence.
5. The system of claim 4, further characterized by
   a. means connecting said power control means and said time-sequenced control means, whereby said power control means is rendered effective simultaneously with the connection in circuit of selected ones of said control resistors.
6. An electronically attenuated system, for a clinical audiometer or the like, for generating an output signal of controllably variable power over a wide power range, which comprises
   a. an output circuit,
   b. means for developing a signal voltage at a predetermined level at least equal to the desired maximum voltage output of the system,
   c. variable signal attenuating means including first common resistor means and a plurality of control resistors selectively connectable in series therewith to effect controllable voltage drop across said first common resistance means, d. said signal attenuating means providing a minimum output signal which is a sufficiently large multiple of the desired output level that the signal to electronic noise ratio permits intelligible, audible reproduction of the signal, e. a high ratio voltage divider connected to said variable signal attenuating means and forming part of the output circuit of said system, and f. power control means selectively operative to effectively by-pass at least part of said voltage divider, at all times when said system is operated at levels of its power range above a predetermined level.

7. An electronically attenuated system according to claim 6, further characterized by a. said variable signal attenuating means comprising a plurality of control resistors of different resistance value connectable selectively in series with said first common resistor, b. a switching transistor connected in series with each of said control resistors, c. sequence control means connected to the base electrode of each of said transistors for selectively rendering the transistors conductive or non-conductive in predetermined sequence, to effect variable, controlled voltage drop across said first common resistor means.

8. An electronically attenuated audiometer of the von Bekesy type adapted to apply to a test subject audible test signals over a range at least ninety decibels, which comprises a. electro-mechanical transducer means for converting electrical signals of a given power level to audible test signals of a related power level.

b. signal generating means for generating an input signal at a power level equal to or greater than the power level required to develop the maximum audible test signal, c. said signal generating means including variable signal attenuating circuit means in its output, d. voltage dividing resistance means connected in series between the output of the signal attenuating circuit means and the electromechanical transducer means and having an effective resistance which is a substantial multiple of the effective resistance of the transducer means, e. said substantial multiple being sufficiently large to enable the minimum signal generated at the output of said attenuating circuit means to have a signal to noise ratio permitting intelligible, audible reproduction of the signal, f. electronically triggered circuit means for neutralizing the voltage dividing effect of said voltage dividing resistance means, g. a first plurality of attenuation control resistors adapted to be selectively connected in said variable signal attenuating circuit means for controllably attenuating the input, in major increments, h. first sequencing means for electronically connecting said first attenuator control resistors selectively in said signal attenuating circuit means for effecting sequential, progressive, major incremental changes in the output power of said signal generating means, i. said first sequencing means including means for automatically activating neutralizing circuit means in conjunction with the connecting in circuit of certain of said attenuator control resistors corresponding to a predetermined higher range of major power increments and automatically deactivating said neutralizing circuit means in conjunction with the connecting in circuit of attenuator control resistors corresponding to a lower range of major power increments, j. a second plurality of attenuator control resistors adapted to be selectively connected in said variable signal attenuating circuit means for effecting controllable signal attenuation in minor increments, and k. second sequencing means for electronically connecting said second attenuator control resistors selectively in said variable signal attenuating means for effecting sequential, progressive minor incremental changes in the output power of said signal generating means over the range of said major increments.

9. An electronically attenuated audiometer according to claim 8, further characterized by a. said signal generating means being adapted to develop a signal corresponding to a predetermined output power level, b. said first plurality of attenuator control resistors comprising five selectively effective resistors operative, when connected, to attenuate said signal in increments of ten decibels, to a predetermined minimum output level c. the second plurality of attenuator control resistors comprising selectively effective resistors operative, when connected, to attenuate said signal in increments of one decibel.

10. A controllably effective voltage divider output for an electronically attenuated audiometer circuit or the like, which comprises a. first and second resistance means connected in series, b. at least a portion of the second resistance means constituting an output load, c. said first resistance being a multiple of the second, d. electronically attenuated power means for supplying power to said voltage divider input, and e. circuit means effective when actuated to effectively neutralize the effect of said first resistance means, f. said circuit means including a unity gain operational amplifier and a transistorized current amplifier.

11. A controllably effective voltage divider output according to claim 10, further characterized by a. said electronically attenuated power means including a plurality of transistor-switched resistors and a similar plurality of switching transistors for effecting controlled attenuation of the input signal, and b. means including the switching transistors for selected ones of said resistors for actuating said circuit means.

12. A signal generating circuit for a clinical audiometer or the like, comprising a. an output load, b. resistance means in series with said output load and forming, in conjunction therewith, a high ratio voltage divider, c. said resistance means including two resistance sections of substantially equal resistance, d. a solid-state amplifier system connected in series with one of said resistance sections and in parallel with the other to form a unity gain operational amplifier, e. said solid state amplifier system including a transistorized current amplifier, f. electronically sequenced variable voltage divider signal attenuation means forming the input to said high ratio voltage divider, and g. means for selectively rendering effective said amplifier system when said variable signal attenuation means is conditioned to provide signals to said output at levels higher than a predetermined level, h. said voltage divider having a sufficiently high ratio to permit intelligible, audible reproduction of the minimum signal level imparted by said attenuation means.

13. The circuit of claim 12, further characterized by said signal attenuation means comprising a two stage attenuation system, b. each of said stages comprising a plurality of resistances connected independently to a like plurality of switching transistors, to provide for signal attenuation in increments of one decibel and increments of ten decibels.

c. separate sequencing circuit means for "units" and "tens" increments, for progressively increasing or decreasing the signal attenuation in increments of one decibel over a substantial range, and d. means for rendering effective said amplifier means when said sequencing circuit means progressively decreases the signal attenuation to a predetermined level.

14. The circuit of claim 13, further characterized by a. chart and stylus means for recording the condition of the circuit, b. a stepping motor and input pulse control for moving said stylus, and c. position responsive means associated with the stylus drive for generating circuit control pulses in response to actual movements of said stylus.

15. The circuit of claim 13, further characterized by a. said sequencing means comprising pulse actuated up/down decade counters and associated BCD-to-decimal converters.

* * * * *